United States Patent
Boudes et al.

(10) Patent No.: US 10,813,896 B2
(45) Date of Patent: *Oct. 27, 2020

(54) TREATMENT OF INTRAHEPATIC CHOLESTATIC DISEASES

(71) Applicant: CymaBay Therapeutics, Inc., Newark, CA (US)

(72) Inventors: Pol Boudes, Fremont, CA (US); Charles A. McWherter, Oakland, CA (US)

(73) Assignee: CymaBay Therapeutics, Inc., Newark, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/676,014

(22) Filed: Nov. 6, 2019

(65) Prior Publication Data

US 2020/0129460 A1   Apr. 30, 2020

Related U.S. Application Data

(63) Continuation of application No. 16/032,380, filed on Jul. 11, 2018, now Pat. No. 10,512,622.

(60) Provisional application No. 62/532,571, filed on Jul. 14, 2017, provisional application No. 62/563,491, filed on Sep. 26, 2017.

(51) Int. Cl.
*A61K 31/192* (2006.01)
*A61P 1/16* (2006.01)
*A61K 9/48* (2006.01)
*A61K 9/00* (2006.01)

(52) U.S. Cl.
CPC .......... *A61K 31/192* (2013.01); *A61K 9/0053* (2013.01); *A61K 9/4858* (2013.01); *A61P 1/16* (2018.01)

(58) Field of Classification Search
CPC .. A61K 31/192; A61K 9/0053; A61K 9/4858; A61P 1/16
See application file for complete search history.

(56) References Cited

U.S. PATENT DOCUMENTS

| | | | |
|---|---|---|---|
| 6,150,371 A | 11/2000 | Fujiwara et al. |
| 7,301,050 B2 | 11/2007 | Kuo et al. |
| 7,635,718 B2 | 12/2009 | Kuo et al. |
| 7,709,682 B2 | 5/2010 | Abdel-Magid et al. |
| 8,106,095 B2 | 1/2012 | Kuo et al. |
| 9,381,181 B2 | 7/2016 | Roberts et al. |
| 9,486,428 B2 | 11/2016 | Boudes et al. |
| 9,616,039 B2 | 4/2017 | Roberts et al. |
| 9,808,436 B2 | 11/2017 | Boudes et al. |
| 9,962,346 B2 | 8/2018 | Roberts et al. |
| 10,188,620 B2 | 1/2019 | Roberts et al. |
| 2006/0160867 A1 | 7/2006 | Freedman |
| 2008/0153882 A1 | 6/2008 | Nishi et al. |
| 2010/0152295 A1 | 6/2010 | Karpf et al. |
| 2015/0139987 A1 | 5/2015 | Martin et al. |
| 2015/0266560 A1 | 9/2015 | Boudes et al. |
| 2015/0290154 A1 | 10/2015 | Roberts et al. |
| 2015/0374649 A1 | 12/2015 | Boudes et al. |
| 2016/0279085 A1 | 9/2016 | Martin et al. |
| 2017/0340589 A1 | 11/2017 | Boudes et al. |
| 2018/0036268 A1 | 2/2018 | Boudes et al. |

FOREIGN PATENT DOCUMENTS

| | | |
|---|---|---|
| WO | 97/45141 A1 | 12/1997 |
| WO | 2007/033231 A2 | 3/2007 |
| WO | 2015/077154 A1 | 5/2015 |
| WO | 2015/143178 A1 | 9/2015 |
| WO | 2015/157697 A1 | 10/2015 |
| WO | 2015/200580 A1 | 12/2015 |
| WO | 2017/200715 A1 | 11/2017 |
| WO | 2017/209865 A1 | 12/2017 |

OTHER PUBLICATIONS

Bays et al., "MBX-8025, A Novel Peroxisome Proliferator Receptor-σ Agonist: Lipid and Other Metabolic Effects in Dyslipidemic Overweight Patients Treated with and without Atorvastatin", J. Clin. Endocrin. Metab., 96(9), 2889-2897 (2011).

Boudes et al., "Treatment of cholestatic pruritus", U.S. Appl. No. 16/140,365, filed Sep. 24, 2018, as yet unpublished.

Boudes et al., "Treatment of intrahepatic cholestatic diseases", U.S. Appl. No. 16/222,325, filed Dec. 17, 2018, as yet unpublished.

Choi et al., "Effects of the PPAR-σ agonist MBX-8025 on atherogenic dyslipidemia", Atherosclerosis, 220, 470-476 (2012).

clinicaltrials.gov, NCT02609048, "Study to Evaluate the Effects of Two Doses of MBX-8025 in Subjects With Primary Biliary Cirrhosis (PBC)", first posted Nov. 13, 2015, URL: https://clinicaltrials.gov/ct2/show/NCT02609048 [provided copy retrieved on Jun. 11, 2016].

clinicaltrials.gov, NCT02955602, "Seladelpar (MBX-8025) in Subjects With Primary Biliary Cholangitis (PBC)", first posted Nov. 2, 2016, URL: https://clinicaltrials.gov/ct2/history/NCT02955602?A=1&B=31&C=Side-by-Side#StudyPageTop [provided copy retrieved on Feb. 6, 2019].

(Continued)

*Primary Examiner* — Sarah Pihonak
(74) *Attorney, Agent, or Firm* — HDC IP Law, LLP; Sam L. Nguyen

(57) ABSTRACT

Treatment of intrahepatic cholestatic diseases by therapy with seladelpar or a salt thereof.

10 Claims, No Drawings

(56) References Cited

OTHER PUBLICATIONS clinicaltrials.gov, NCT03301506, "Seladelpar in Subjects With Primary Biliary Cholangitis (PBC)", first posted Oct. 4, 2017, URL: https://clinicaltrials.gov/ct2/show/NCT03301506 [provided copy retrieved on Feb. 17, 2019].

clinicaltrials.gov, NCT03602560, "Seladelpar in Subjects With Primary Biliary Cholangitis (PBC) and an Inadequate Response to or an Intolerance to Ursodeoxycholic Acid (UDCA)", first posted Jul. 27, 2018, URL: https://clinicaltrials.gov/ct2/show/NCT03602560 [provided copy retrieved on Feb. 17, 2019].

clinicaltrialsregister.eu, "A study evaluating the safety and efficacy of MBX-8025 in subjects with Primary Biliary Cholangitis (PBC) and an inadequate response to or intolerance to ursodeoxycholic acid (UDCA)", first entered Nov. 17, 2016, URL: https://www.clinicaltrialsregister.eu/ctr-search/trial/2016-002996-91/DE [provided copy retrieved on Feb. 6, 2019].

Iwaisako et al., "Protection from liver fibrosis by a peroxisome proliferator-activated receptor σ agonist", Proc. Nat. Acad. Sci., 109(2), E1369-E1376 (2012).

Jones et al.,"Seladelpar (MBX-8025), a selective PPAR-94 agonist, in patients with primary biliary cholangitis with an inadequate response to ursodeoxycholic acid: a double-blind, randomised, placebo-controlled, phase 2, proof-of-concept study", Lancet Gastroenterol. Hepatol., 2(10), 716-726 (2017), published online Aug. 14, 2017.

Li, ed., "Artificial Liver", 2nd edition, Zhejian University Press,Sep. 2012, pp. 58 and 59, "4. Enzymes indicative of cholestasis". (Translation provided).

Lindor et al., "AASLD Guidelines: Primary Biliary Cirrhosis", Hepatology, 50, 291-308 (2009).

Martin et al., "Treatment of NAFLD and NASH", U.S. Appl. No. 16/222,379, filed Dec. 17, 2018, as yet unpublished.

patient.info, "Primary Biliary Cirrhosis", URL: http://patient.info/doctor/primary-biliary-cirrhosis-pro; accessed Feb. 17, 2016.

Vroon et al., "Alkaline Phosphatase and Gamma Glutamyltransferase", article at pp. 494-496 of Walker et al., ed., "Clinical Methods: The History, Physical, and Laboratory Examinations", 3rd ed., Butterworths (Boston), 1990. ISBN-10: 0-409-90077-X.

Wikipedia, "Cholestasis", Jun. 11, 2013, URL: http://en.wikipedia.org/w/index.php?title=Cholestasis&oldid=559348356.

TREATMENT OF INTRAHEPATIC CHOLESTATIC DISEASES

CROSS-REFERENCE TO RELATED APPLICATIONS

This application is a continuation of application Ser. No. 16/032,380, filed 11 Jul. 2018, entitled "Treatment of intrahepatic cholestatic diseases". Application Ser. No. 16/032,380 claims the priority under 35 USC 119(e) of Applications Nos. 62/532,571, filed 14 Jul. 2017, and 62/563,491, filed 26 Sep. 2017, both entitled "Treatment of intrahepatic cholestatic diseases". The entire disclosures of both of those provisional applications have been incorporated into application Ser. No. 16/032,380 by reference.

BACKGROUND OF THE INVENTION

Field of the Invention

This invention relates to the treatment of intrahepatic cholestatic diseases.

Description of the Related Art

Intrahepatic Cholestatic Diseases

Cholestasis is a condition in which the flow of bile from the liver to the duodenum is slowed or blocked. Cholestasis may be divided conveniently into two types: intrahepatic cholestasis, inside the liver, where bile formation is disturbed by conditions such as various diseases, extended intravenous nutrition, or as a side effect of certain drugs (such as some antibiotics); and extrahepatic cholestasis, occurring outside the liver, typically where the flow of bile is obstructed by a mechanical partial or complete closure of the bile duct, such as by bile duct tumors, cysts, bile duct stones, strictures, or pressure on the bile duct; though primary sclerosing cholangitis (PSC) may be intrahepatic or extrahepatic. Common symptoms of cholestasis include fatigue, pruritus (itching), jaundice, and xanthoma (deposits of cholesterol-rich material under the skin). The effects of cholestasis are profound and widespread, leading to worsening liver disease with systemic illness, liver failure, and the need for liver transplantation.

Intrahepatic cholestatic diseases include, in order of decreasing frequency, primary biliary cholangitis (PBC, formerly known as primary biliary cirrhosis), primary sclerosing cholangitis (PSC), progressive familial intrahepatic cholestasis (PFIC), and Alagille syndrome (AS).

PBC is an autoimmune disease of the liver marked by the slow progressive destruction of the small bile ducts of the liver, with the intralobular ducts affected early in the disease. When these ducts are damaged, bile builds up in the liver (cholestasis) and over time damages the tissue, which can lead to scarring, fibrosis and cirrhosis. Recent studies have shown that it may affect up to 1 in 3,000-4,000 people, with a sex ratio at least 9:1 female to male. There is no cure for PBC, and liver transplantation often becomes necessary; but medication such as ursodeoxycholic acid (UDCA, ursodiol) to reduce cholestasis and improve liver function, cholestyramine to absorb bile acids, modafinil for fatigue, and fat-soluble vitamins (vitamins A, D, E, and K, since reduced bile flow makes it difficult for these vitamins to be absorbed) may slow the progression to allow a normal lifespan and quality of life. UDCA is approved in the United States to treat PBC. Japanese researchers have reported that the addition of bezafibrate, a peroxisome proliferator-activated receptor (PPAR) pan-agonist and pregnane X receptor agonist, to UDCA is helpful in treating patients who are refractory to UDCA monotherapy, improving serum biliary enzymes, cholesterol (C), and triglycerides (TGs). Obeticholic acid (OCA, 6α-ethylchenodeoxycholic acid), a semisynthetic bile acid analog that is a highly potent farnesoid X receptor agonist, was approved in 2016 in the United States for the treatment of PBC, either in addition to UDCA or as sole treatment when UDCA is not tolerated.

PSC is a chronic cholestatic liver disease characterized by intra- or extrahepatic biliary duct inflammation and fibrosis, eventually leading to cirrhosis. The underlying cause of the inflammation is believed to be autoimmunity; and about three-fourths of patients with PSC have inflammatory bowel disease, usually ulcerative colitis, though this is reported to vary by country, as is the prevalence (generally reported at about 1 in 10,000) and sex ratio (generally reported as predominately male). Standard treatment includes UDCA, which has been shown to lower elevated liver enzyme numbers in people with PSC, but has not improved liver survival or overall survival; and also includes antipruritics, cholestyramine, fat-soluble vitamins, and antibiotics to treat infections (bacterial cholangitis). In a study reported in 2009, long-term high-dose UDCA therapy was associated with improvement in serum liver tests in PSC but did not improve survival and was associated with higher rates of serious adverse events. Liver transplantation is the only proven long-term treatment.

PFIC refers to a group of three types of autosomal recessive disorders of childhood associated with intrahepatic cholestasis: deficiency of familial intrahepatic cholestasis 1 (PFIC-1), deficiency of bile salt export pump (PFIC-2), and deficiency of multidrug resistance protein 3 (PFIC-3). They have a combined incidence of 1 in 50,000-100,000. The onset of the disease is usually before age 2, with PFIC-3 usually appearing earliest, but patients have been diagnosed with PFIC even into adolescence. Patients usually show cholestasis, jaundice, and failure to thrive; and intense pruritus is characteristic. Fat malabsorption and fat-soluble vitamin deficiency may appear. Biochemical markers include a normal γ-glutamyl transpeptidase (GGT) in PFIC-1 and PFIC-2, but a markedly elevated GGT in PFIC-3; while serum bile acid levels are greatly elevated; though serum cholesterol levels are typically not elevated, as is seen usually in cholestasis, because the disease is due to a transporter as opposed to an anatomical problem with biliary cells. The disease is typically progressive without liver transplantation, leading to liver failure and death in childhood; and hepatocellular carcinoma may develop in PFIC-2 at a very early age. Medication with UDCA is common; supplemented by fat-soluble vitamins, cholestyramine, and pancreatic enzymes in PFIC-1.

AS, also known as Alagille-Watson syndrome, syndromic bile duct paucity, and arteriohepatic dysplasia, is an autosomal dominant disorder associated with liver, heart, eye and skeletal abnormalities, as well as characteristic facial features; with an incidence of about 1 in 100,000. The liver abnormalities are narrowed and malformed bile ducts within the liver; and these result in obstruction of bile flow, causing cirrhosis (scarring) of the liver. AS is predominately caused by changes in the Jagged1 gene, located on chromosome 20. In 3-5% of cases, the entire gene is deleted (missing) from one copy of chromosome 20; in the remainder, there are changes or mutations in the Jagged1 DNA sequence. In a very small number of cases, less than 1 percent, changes in another gene, Notch2, result in AS. In about one-third of the cases, the mutation is inherited; in about two-thirds, the mutation is new in that case. There is no cure for AS, though the severity of liver disease typically peaks by 3 to 5 years of age and often resolves by 7 to 8 years of age. In some people, the hepatic disease will progress to end-stage liver disease and may require liver transplantation; approximately 15% of patients with AS require liver transplantation. A number of different medications, for example UDCA, have been used to improve bile flow and reduce itching, and many patients are given high doses of fat-soluble vitamins.

Alkaline phosphatase (ALP) and GGT are key markers of cholestasis. While an elevation of one of them alone does not indicate cholestasis, and other parameters would be needed for confirmation, elevation in both ALP and GGT is indicative of cholestasis; and a decrease in both indicates improvement of cholestasis. Thus ALP and GGT levels serve as biochemical markers for the presence of biliary pathophysiology present in intrahepatic cholestatic diseases, and ALP level has been used as a primary outcome marker in clinical studies of intrahepatic diseases such as PBC (including in the studies leading to US approval of OCA).

Treatments for Intrahepatic Cholestatic Diseases

As mentioned above, UDCA is a common treatment for intrahepatic cholestatic diseases, because of its action in reducing cholestasis and improving liver function. However, a Cochrane Review of UDCA in PBC in 2012 found that, although UDCA showed a reduction in biomarkers of liver pathology, jaundice, and ascites, there was no evidence in the medical literature for any benefit of UDCA on mortality or liver transplantation, while its use was associated with weight gain and costs. Also, as mentioned above, OCA was approved in 2016 in the United States for the treatment of PBC, either in addition to UDCA or as sole treatment when UDCA is not tolerated. While UDCA is also used in other intrahepatic cholestatic diseases, the only long-term treatment for many patients with intrahepatic cholestatic diseases is liver transplantation.

It would be desirable to develop pharmacological treatments for intrahepatic cholestatic diseases.

Seladelpar

Seladelpar (International Nonproprietary Name—INN) has the chemical name [4-({(2R)-2-ethoxy-3-[4-(trifluoromethyl)phenoxy]propyl}sulfanyl)-2-methylphenoxy] acetic acid [IUPAC name from WHO Recommended INN: List 77], and the code number MBX-8025. Seladelpar and its synthesis, formulation, and use are disclosed in, for example, U.S. Pat. No. 7,301,050 (compound 15 in Table 1, Example M, claim 49), U.S. Pat. No. 7,635,718 (compound 15 in Table 1, Example M), and U.S. Pat. No. 8,106,095 (compound 15 in Table 1, Example M, claim 14). Lysine (L-lysine) salts of seladelpar and related compounds are disclosed in U.S. Pat. No. 7,709,682 (seladelpar L-lysine salt throughout the Examples, crystalline forms claimed).

Seladelpar is an orally active, potent (2 nM) agonist of peroxisome proliferator-activated receptor-δ (PPARδ). It is specific (>600-fold and >2500-fold compared with PPARα and PPARγ receptors). PPARδ activation stimulates fatty acid oxidation and utilization, improves plasma lipid and lipoprotein metabolism, glucose utilization, and mitochondrial respiration, and preserves stem cell homeostasis. According to U.S. Pat. No. 7,301,050, PPARδ agonists, such as seladelpar, are suggested to treat PPARδ-mediated conditions, including "diabetes, cardiovascular diseases, Metabolic X syndrome, hypercholesterolemia, hypo-high density lipoprotein (HDL)-cholesterolemia, hyper-low density protein (LDL)-cholesterolemia, dyslipidemia, atherosclerosis, and obesity", with dyslipidemia said to include hypertriglyceridemia and mixed hyperlipidemia.

A Phase 2 study of seladelpar L-lysine dihydrate salt in mixed dyslipidemia (6 groups, 30 subjects/group: once daily oral placebo, atorvastatin (ATV) 20 mg, or seladelpar L-lysine dihydrate salt at 50 or 100 mg (calculated as the free acid) capsules alone or combined with ATV 20 mg, for 8 weeks) has been reported by Bays et al., "MBX-8025, A Novel Peroxisome Proliferator Receptor-δ Agonist: Lipid and Other Metabolic Effects in Dyslipidemic Overweight Patients Treated with and without Atorvastatin", *J. Clin. Endocrin. Metab.*, 96(9), 2889-2897 (2011) and Choi et al., "Effects of the PPAR-6 agonist MBX-8025 on atherogenic dyslipidemia", *Atherosclerosis,* 220, 470-476 (2012). Compared to placebo, seladelpar alone and in combination with ATV significantly ($P<0.05$) reduced apolipoprotein B-100 by 20-38%, LDL by 18-43%, triglycerides (TGs) by 26-30%, non-HDL-C by 18-41%, free fatty acids by 16-28%, and high-sensitivity C-reactive protein (hs-CRP) by 43-72%; it raised HDL-C by 1-12% and also reduced the number of patients with the metabolic syndrome and a preponderance of small LDL particles. Seladelpar significantly reduced ALP by 32-43%, compared to reductions of only 4% in the control group and 6% in the ATV group; and significantly reduced GGT by 24-28%, compared to a reduction of only 3% in the control group and an increase of 2% in the ATV group.

US Patent Application Publication No. US 2015/0265560 A1 and PCT International Publication No. WO 2015/143178 A1 disclose the treatment of intrahepatic cholestatic diseases, such as PBC, PSC, PFIC, and AS with seladelpar; and US Patent Application Publication No. US 2017/0340589 A1 and PCT International Publication No. WO 2017/209865 A1 disclose the treatment of intrahepatic cholestatic diseases, such as PBC, PSC, PFIC, and AS with low doses of seladelpar.

The entire disclosures of the documents referred to in this application are incorporated into this application by reference.

SUMMARY OF THE INVENTION

This invention is a method of treatment of an intrahepatic cholestatic disease comprising administration of a compound that is seladelpar or a salt thereof in an amount between 0.5 mg/day and 20 mg/day; such as at 0.5, 1, or 2 mg/day.

Seladelpar has already been demonstrated to be effective in the treatment of PBC at doses of 50 mg/day and 200 mg/day. It is also effective in much lower dosages, such as 5 mg/day and 10 mg/day. Similarly, it is expected to be useful in other intrahepatic cholestatic diseases at similar dosages.

Because seladelpar lowers ALP and GGT, which are elevated in intrahepatic cholestatic diseases, its use will result in a reduction in cholestasis and provide an effective treatment for these diseases.

Preferred embodiments of this invention are characterized by the specification and by the features of claims 1 to 17 of this application as filed.

DETAILED DESCRIPTION OF THE INVENTION

Definitions

"Intrahepatic cholestatic diseases" and their treatment are described in the subsections entitled "Intrahepatic cholestatic diseases" and "Treatments for intrahepatic cholestatic diseases" of the Background of the invention.

"Treating" or "treatment" of an intrahepatic cholestatic disease in a human includes one or more of:

(1) preventing or reducing the risk of developing an intrahepatic cholestatic disease, i.e., causing the clinical symptoms of an intrahepatic cholestatic disease not to develop in a subject who may be predisposed to an intrahepatic cholestatic disease but who does not yet experience or display symptoms of the intrahepatic cholestatic disease (i.e. prophylaxis);

(2) inhibiting an intrahepatic cholestatic disease, i.e., arresting or reducing the development of the intrahepatic cholestatic disease or its clinical symptoms; and (3) relieving an intrahepatic cholestatic disease, i.e., causing regression, reversal, or amelioration of the intrahepatic cholestatic disease or reducing the number, frequency, duration or severity of its clinical symptoms.

A "therapeutically effective amount" of seladelpar or a seladelpar salt means that amount which, when administered to a human for treating an intrahepatic cholestatic disease, is sufficient to effect treatment for the intrahepatic cholestatic disease. The therapeutically effective amount for a particular subject varies depending upon the age, health and physical condition of the subject to be treated, the intrahepatic cholestatic disease and its extent, the assessment of the medical situation, and other relevant factors. It is expected that the therapeutically effective amount will fall in a relatively broad range that can be determined through routine trial.

"Seladelpar" is described in the subsection entitled "Seladelpar" of the BACKGROUND OF THE INVENTION.

Salts (for example, pharmaceutically acceptable salts) of seladelpar are included in this invention and are useful in the methods described in this application. These salts are preferably formed with pharmaceutically acceptable acids. See, for example, "Handbook of Pharmaceutically Acceptable Salts", Stahl and Wermuth, eds., Verlag Helvetica Chimica Acta, Zürich, Switzerland, for an extensive discussion of pharmaceutical salts, their selection, preparation, and use. Unless the context requires otherwise, reference to seladelpar is a reference both to the compound and to its salts.

Because seladelpar contains a carboxyl group, it may form salts when the acidic proton present reacts with inorganic or organic bases. Typically seladelpar is treated with an excess of an alkaline reagent, such as hydroxide, carbonate or alkoxide, containing an appropriate cation. Cations such as $Na^+$, $K^+$, $Ca^{2+}$, $Mg^{2+}$, and $NH_4^+$ are examples of cations present in pharmaceutically acceptable salts. Suitable inorganic bases, therefore, include calcium hydroxide, potassium hydroxide, sodium carbonate and sodium hydroxide. Salts may also be prepared using organic bases, such as salts of primary, secondary and tertiary amines, substituted amines including naturally-occurring substituted amines, and cyclic amines, including isopropylamine, trimethylamine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, N-ethylpiperidine, and the like. As noted in the "Seladelpar" subsection, seladelpar is currently formulated as its L-lysine dihydrate salt.

"Comprising" or "containing" and their grammatical variants are words of inclusion and not of limitation and mean to specify the presence of stated components, groups, steps, and the like but not to exclude the presence or addition of other components, groups, steps, and the like. Thus, "comprising" does not mean "consisting of", "consisting substantially of", or "consisting only of"; and, for example, a formulation "comprising" a compound must contain that compound but also may contain other active ingredients and/or excipients.

Formulation and Administration

Seladelpar may be administered by any route suitable to the subject being treated and the nature of the subject's condition. Routes of administration include administration by injection, including intravenous, intraperitoneal, intramuscular, and subcutaneous injection, by transmucosal or transdermal delivery, through topical applications, nasal spray, suppository and the like or may be administered orally. Formulations may optionally be liposomal formulations, emulsions, formulations designed to administer the drug across mucosal membranes or transdermal formulations. Suitable formulations for each of these methods of administration may be found, for example, in "Remington: The Science and Practice of Pharmacy", 20th ed., Gennaro, ed., Lippincott Williams & Wilkins, Philadelphia, Pa., U.S.A. Because seladelpar is orally available, typical formulations will be oral, and typical dosage forms will be tablets or capsules for oral administration. As mentioned in the "Seladelpar" subsection, seladelpar has been formulated in capsules for clinical trials.

Depending on the intended mode of administration, the pharmaceutical compositions may be in the form of solid, semi-solid or liquid dosage forms, preferably in unit dosage form suitable for single administration of a precise dosage. In addition to an effective amount of seladelpar, the compositions may contain suitable pharmaceutically-acceptable excipients, including adjuvants which facilitate processing of the active compounds into preparations which can be used pharmaceutically. "Pharmaceutically acceptable excipient" refers to an excipient or mixture of excipients which does not interfere with the effectiveness of the biological activity of the active compound(s) and which is not toxic or otherwise undesirable to the subject to which it is administered.

For solid compositions, conventional excipients include, for example, pharmaceutical grades of mannitol, lactose, starch, magnesium stearate, sodium saccharin, talc, cellulose, glucose, sucrose, magnesium carbonate, and the like. Liquid pharmacologically administrable compositions can, for example, be prepared by dissolving, dispersing, etc., an active compound as described herein and optional pharmaceutical adjuvants in water or an aqueous excipient, such as, for example, water, saline, aqueous dextrose, and the like, to form a solution or suspension. If desired, the pharmaceutical composition to be administered may also contain minor amounts of nontoxic auxiliary excipients such as wetting or emulsifying agents, pH buffering agents and the like, for example, sodium acetate, sorbitan monolaurate, triethanolamine sodium acetate, triethanolamine oleate, etc.

For oral administration, the composition will generally take the form of a tablet or capsule; or, especially for pediatric use, it may be an aqueous or nonaqueous solution, suspension or syrup. Tablets and capsules are preferred oral administration forms. Tablets and capsules for oral use will generally include one or more commonly used excipients such as lactose and corn starch. Lubricating agents, such as magnesium stearate, are also typically added. When liquid suspensions are used, the active agent may be combined with emulsifying and suspending excipients. If desired, flavoring, coloring and/or sweetening agents may be added as well. Other optional excipients for incorporation into an oral formulation include preservatives, suspending agents, thickening agents, and the like.

Typically, a pharmaceutical composition of seladelpar, or a kit comprising compositions of seladelpar, is packaged in a container with a label, or instructions, or both, indicating use of the pharmaceutical composition or kit in the treatment of an intrahepatic cholestatic disease.

A suitable (i.e. a therapeutically effective) amount of seladelpar or a salt thereof for oral dosing, when the amount is calculated as seladelpar, is expected to be at least 0.5 mg/day, for example at least 1 mg/day, such as at least 2 mg/day; but not more than 25 mg/day, for example not more than 15 mg/day, or not more than 10 mg/day; for example 1 mg/day, 2 mg/day, 5 mg/day, or 10 mg/day, for an adult subject with an intrahepatic cholestatic disease, depending on the extent and severity of the disease and stage of disease, and factors such as hepatic and renal function. That is, a suitable amount of seladelpar for oral dosing for adults in diseases such as PSC and PBC is expected to be below the low end of the amounts employed in Example 1 but include the amounts employed in Example 2. Suitable reductions in dose toward or below the lower end of the outer range above may be made for subjects who are children in diseases such as PFIC and AS, depending on such additional factors as age and body mass; and in subjects with significant hepatic impairment, such as subjects in Child-Pugh classes B and C [see, for example, the Wikipedia article "Child-Pugh Score", https://en.wikipedia.org/wiki/Child-Pugh_score], depending on the degree of impairment, because a study has suggested a significant increase in the maximum plasma concentration of seladelpar and an increase in the area-under-the-curve exposure for seladelpar and two of its three principal metabolites in these groups. These amounts represent an average daily dose, and not necessarily an amount given at a single dose. Dosing may be as frequent as more than once/day (where the amount, or daily dose, will be divided between the number of administrations per day), but will more typically be once/day (where the amount is given in a single administration). Optionally, particularly in cases of significant hepatic impairment, the dosing may be less frequent than once/day, such as between once/week and every other day, for example once/week, twice/week (especially with the doses at least three days apart), three times/week (especially with the doses at least two days apart), or every other day; so that, as an example, a subject may receive 5 mg twice/week for an amount (daily dose) of 1.4 mg/day.

A person of ordinary skill in the art of the treatment of intrahepatic cholestatic disease will be able to ascertain a therapeutically effective amount of seladelpar or a seladelpar salt for a particular disease, stage of disease, and patient to achieve a therapeutically effective amount without undue experimentation and in reliance upon personal knowledge and the disclosure of this application.

EXAMPLES

Example 1: High Dose Trial in PBC
(NCT02609048)

The trial subjects were adult, male or female, with a diagnosis of PBC by at least two of the following three criteria: (a) a history of alkaline phosphatase (ALP) above the upper limit of normal (ULN) for at least six months, (b) positive anti-mitochondrial antibody titers >1/40 on immunofluorescence or M2 positive by enzyme linked immunosorbent assay or positive PBC-specific antinuclear antibodies, and (c) documented liver biopsy result consistent with PBC, on a stable and recommended dose of UDCA for the past twelve months or UDCA intolerant, and ALP≥1.67× ULN. Exclusion criteria included AST or ALT≥3×ULN, total bilirubin (TBIL)≥2×ULN, autoimmune hepatitis or a history of chronic viral hepatitis, PSC, the current use of fibrates or simvastatin, the use of colchicine, methotrexate, azathioprine, or systemic steroids in the previous two months, the use of an experimental treatment for PBC, and the use of an experimental or unapproved immunosuppressant. The primary study endpoint was decrease in ALP, and the secondary endpoint was the responder rate for subjects achieving ALP<1.67×ULN and total bilirubin within normal limit, and >15% decrease in ALP. Additional secondary endpoints were changes in GGT, TBIL, and 5'-nucleotidase, which are other recognized biochemical markers of cholestasis. Subjects were randomized to receive either placebo, 50 mg/day, or 200 mg/day of seladelpar as the L-lysine dihydrate salt orally once/day in capsule form for 12 weeks. During the study, three cases of asymptomatic increases in transaminases were observed (two in the 200 mg and one in the 50 mg groups). All three were reversible on cessation of treatment and were not accompanied by elevation of TBIL. Since the study had already shown a clear efficacy signal, the study was discontinued. After the study was unblinded, changes in the primary endpoint ALP were analyzed using data available for the 26 subjects (10 in the placebo group, 9 in the 50 mg/day seladelpar group, and 7 in the 200 mg/day seladelpar group) enrolled in the study and completing at least two weeks of treatment. According to the original statistical plan, changes in ALP were calculated using the last observation carried forward. The mean decreases from baseline in ALP for the 50 mg/day and 200 mg/day dose groups were 57% and 62%, respectively, compared with 0.37% for placebo ($p<0.0001$ for both). The responder rates for the placebo, 50 mg/day, and 200 mg/day groups were 10%, 67% and 100%, respectively, despite the baseline ALP levels being different at 239, 313, and 280 U/L. The p-values comparing the responder rates for the 50 mg/day and 200 mg/day groups with placebo were 0.020 and 0.0004 (Fisher's Exact Test), respectively. Thus, seladelpar exhibits a rapid and potent anti-cholestatic effect in subjects with PBC. The lack of a dose response suggested that lower doses could be effective as well. Since a recently completed preclinical study with seladelpar showed that the main route of elimination of the drug is through bile and that the drug is concentrated in bile, and since subjects with PBC have impaired bile flow, the exposure of the drug to the liver in subjects with PBC could have been higher than in prior clinical studies in subjects with normal liver function, explaining both the more potent anticholestatic effect and the transaminase effects. The subjects receiving seladelpar also demonstrated improvements in metabolic parameters, including reductions of LDL-C of 16 and 26% for the 50 mg/day and 200 mg/day dose groups, respectively, vs. 0.8% for placebo after two weeks of dosing. It is also noteworthy that, despite the potent anti-cholestatic effect, no adverse events of pruritus were reported on treatment.

Example 2: Low-Dose Trial in PBC
(NCT02955602)

This example describes a study like that of Example 1, but using doses of 2, 5, or 10 mg/day of seladelpar as the L-lysine dihydrate salt orally once/day in capsule form. In the main study, running for 12 weeks, subjects were to receive either 2, 5, or 10 mg/day; while in an extension study, running for an additional 40 weeks, subjects in the 2 mg/day group were allowed to continue at the 2 mg/day dose or shift to either 5 or 10 mg/day, subjects in the 5 mg/day group were allowed to continue at the 5 mg/day dose or shift to 10 mg/day, and subjects in the 10 mg/day group were allowed to continue at the 10 mg/day dose or shift to 5 mg/day. At baseline (the mean of the screening values and the value at day 1), the subjects had the following values, with numbers in parentheses denoting standard deviations:

| Population | Normal range | 2 mg | 5 mg | 10 mg |
|---|---|---|---|---|
| N | | 11 | 30 | 30 |
| Age, years | | 55 (10) | 57 (8) | 56 (9) |
| Sex, F/M | | 11/0 | 30/0 | 27/3 |
| BMI, Kg/m$^2$ | | 29 (7) | 27 (7) | 26 (5) |
| History of pruritus | | 7 | 19 | 22 |
| ALP (U/L) | 37-116 | 300 (121) | 310 (152) | 265 (83) |
| GGT (U/L) | 7-38 | 255 (143) | 201 (141) | 254 (185) |
| ALT (U/L) | 6-41 | 54 (25) | 40 (22) | 49 (25) |
| TBIL (mg/dL) | 0.1-1.1 | 0.60 (0.12) | 0.68 (0.35) | 0.84 (0.34) |
| Albumin (g/dL) | 3.5-5.5 | 4.1 (0.2) | 4.0 (0.4) | 4.1 (0.3) |
| UDCA dose, mg/Kg | | 14 (4) | 15 (3) | 17 (6) |

The study has now been analyzed through 26 weeks: the 12 weeks of the main study and 14 weeks of the extension study.

The week 12 cohort consisted of 6 subjects in the 2 mg/day group, 25 subjects in the 5 mg/day group, and 22 subjects in the 10 mg/day group. The mean reduction in ALP at 12 weeks was 21% for the 2 mg/day group, 33% for the 5 mg/day group, and 45% for the 10 mg/day group. The mean reduction in ALT at 12 weeks was 9% for the 2 mg/day group, 28% for the 5 mg/day group, and 35% for the 10 mg/day group.

The week 26 cohort consisted of 4 subjects in the 2 or 2 to 5 mg/day group, 13 subjects in the 5 mg/day group, 6 subjects in the 5 to 10 mg/day group, and 19 subjects in the 10 mg/day group. The mean reduction in ALP at 26 weeks was 45% for the 5 mg/day group, 43% for the 5 to 10 mg/day group, and 43% for the 10 mg/day group. At 26 weeks, combining the 5 mg/day and 5 to 10 mg/day groups into a single group for analysis, there were 19 subjects in the combined group and 19 in the 10 mg/day group. Of the combined group, 13 (68%) had ALP≤1.67×ULN, 18 (95%) had a decrease in ALP of ≥15%, and 18 (95%) had TBIL≤ULN, while 5 (26%) had ALP≤ULN. Of the 10 mg/day group, 15 (79%) had ALP≤1.67×ULN, 17 (89%) had a decrease in ALP of ≥15%, and 17 (89%) had a TBIL≤ULN, while 6 (32%) had ALP≤ULN. The mean reduction in ALT at 26 weeks was 40% for the combined group and 43% for the 10 mg/day group.

As of the analysis, there had been 6 serious adverse events, all deemed unrelated to seladelpar, and 2 adverse events leading to seladelpar discontinuation, both deemed unrelated to seladelpar. No transaminase safety signals, and no signals for drug-induced pruritus, were seen.

Example 3: Trial in PSC

Adult subjects with an intrahepatic cholestatic disease such as PSC are treated orally with doses of 1, 2, 5, and 10 mg/day of seladelpar. Subjects are permitted their usual other medications, including UDCA. The subjects are assessed before the study, and at intervals during the study, such as every 4 weeks during the study and 4 weeks after the last dose of the seladelpar therapy, for safety and pharmacodynamic evaluations. At each visit, after a 12-hour fast, blood is drawn and urine collected; and a standard metabolic panel, complete blood count, and standard urinalysis are performed. Blood is analyzed for TC, HDL-C, TG, VLDL-C, LDL-C, and apolipoprotein B, for liver function markers such as total and bone-specific ALP, for GGT, and also for total and conjugated bilirubin. The subjects also maintain health diaries, which are reviewed at each visit. The subjects show an improvement in their disease, as manifested by, for example, a decrease in ALP and GGT.

While this invention has been described in conjunction with specific embodiments and examples, it will be apparent to a person of ordinary skill in the art, having regard to that skill and this disclosure, that equivalents of the specifically disclosed materials and methods will also be applicable to this invention; and such equivalents are intended to be included within the following claims.

What is claimed is:

1. A method of treating primary sclerosing cholangitis by administering a therapeutically effective amount of a compound that is seladelpar or a salt thereof, where the amount of the compound is between 0.5 mg/day and 2 mg/day when the amount of the compound is calculated as seladelpar.

2. The method of claim 1 where the compound is administered orally.

3. The method of claim 1 where the amount of the compound is 0.5 mg/day, 1 mg/day, or 2 mg/day.

4. The method of claim 3 where the amount of the compound is 0.5 mg/day.

5. The method of claim 3 where the amount of the compound is 1 mg/day.

6. The method of claim 3 where the amount of the compound is 2 mg/day.

7. The method of claim 1 where the compound is administered once/day.

8. The method of claim 1 where the compound is administered between once/week and every other day.

9. The method of claim 1 where the compound is a seladelpar L-lysine salt.

10. The method of claim 9 where the compound is seladelpar L-lysine dihydrate salt.

* * * * *